United States Patent
Huang et al.

(10) Patent No.: US 8,017,821 B2
(45) Date of Patent: Sep. 13, 2011

(54) PROCESS FOR ISOMERIZATION OF TETRAHYDRODICYCLOPENTADIENE USING SUPPORTED ACIDIC IONIC LIQUID AS A CATALYST

(75) Inventors: Ming-Yu Huang, Chia-Yi (TW); Jann-Chen Lin, Chia-Yi (TW); Kun-Hai Lin, Chia-Yi (TW); Jung-Chung Wu, Chia-Yi (TW)

(73) Assignee: CPC Corporation, Taiwan, Taipei (TW)

( * ) Notice: Subject to any disclaimer, the term of this patent is extended or adjusted under 35 U.S.C. 154(b) by 396 days.

(21) Appl. No.: 12/410,077

(22) Filed: Mar. 24, 2009

(65) Prior Publication Data

US 2010/0249475 A1    Sep. 30, 2010

(51) Int. Cl.
*C07C 5/25* (2006.01)
(52) U.S. Cl. ............... 585/363; 585/377; 585/669
(58) Field of Classification Search .............. None
See application file for complete search history.

(56) References Cited

U.S. PATENT DOCUMENTS

| | | | |
|---|---|---|---|
| 3,381,046 A | 4/1968 | Cohen et al. | |
| 4,086,284 A | 4/1978 | Schneider et al. | |
| 4,270,014 A * | 5/1981 | Norton et al. | 585/22 |
| 6,969,693 B2 | 11/2005 | Sauvage et al. | |
| 7,488,860 B2 * | 2/2009 | Huang et al. | 585/363 |
| 7,744,838 B2 * | 6/2010 | Davis, Jr. | 423/220 |

OTHER PUBLICATIONS

Misono, M. et al.,"Solid superacid catalysts," Chemtech, Nov. 1993, pp. 23-29.
Rao, P. et al., "Solid-acid alkylation process development is at a crucial stage," Oil & Gas J., Sep. 1996, pp. 56-61.
Weitkamp, J.et al.,"Isobutane/butene alkylation on solid catalysts. Where do we stand?," Catalysis Today, 1999, pp. 193-199, vol. 49).
Getty, E. et al., "Preparation, Characterization, and Catalytic Activity of a New Solid Acid Catalyst System," Inorg. Chem., 1990, pp. 1186-1192, vol. 29.
Hu, X. et al., "Room temperature synthesis of diphenylmethane over MCM-41 supported AlCl3 and other Lewis Acids," , Applied Catalysis, 2001, pp. 1-9, vol. 217.
Drago et al., "Preparation and Catalytic Activity of a New Solid Acid Catalyst," J. Am. Chem. Soc., 1988, pp. 3311-3312, vol. 110.
Clark, J. H. et al., "Environmentally Friendly Catalysis using Supported Reagents; Evolution of a Highly Active Form of Immobilized Aluminum Chloride," J. Chem. Soc., Chem. Commun., 1995, pp. 2037-2040.
Fuentes, G. A. et al., "n-Butane Isomerization Catalyzed by Supported Aluminum Chloride," J. Catalysis, 1982, pp. 436-444, vol. 78.
Jun, S., "Aluminum Impregnation into Mesoporous Silica Molecular Sieves for Catalytic Application to Friedel-Crafts Alkylation" J. Catalysis, 2000, pp. 237-243, vol. 195.
Hu, X.,"Pore Size Engineering on MCM-41: Selectivity Tuning of Heterogenized AlCl3 for the Synthesis of Linear Alkyl Benzenes," J. Catalysis, 2000,vol. 195.
Xue, H., et al, "Progress on Preparation and Application of Supported Lewis Acid Catalysts," Petrochemical Technology, 2006, pp. 88-93, vol. 35.
Wu, J. et al., "The Application of Supported Ionic Liquid on Catalytic Reactions," Journal of Petroleum, pp. 25-34, Dec. 2005, vol. 41 No. 4.
Decastro, C. et al., "Immobilized Ionic Liquids as Lewis Acid Catalysts for the Alkylation of Aromatic Compounds with Dodecene," J. Catalysis, pp. 86-94, vol. 196, 2000.
Valkenberg, M. H. et al., "Immobilization of ionic liquids on solid supports," , Green Chem., 2002, pp. 88-93, vol. 4.
Kang, K.K. et al., "Ionic Liquids Supported on Mesocellular Foam Silica (MCF) and Its Catalytic Activity," J. Chin. Inst. Chem. Engrs., 2006, vol. 37No. 1.

* cited by examiner

*Primary Examiner* — Tam M Nguyen
(74) *Attorney, Agent, or Firm* — Muncy, Geissler, Olds & Lowe, PLLC

(57) ABSTRACT

A process for isomerization of tetrahydrodicyclopentadiene using a supported acidic ionic liquid as catalyst is provided. In the presence of the supported acidic ionic liquid, endo-tetrahydrodicyclopentadiene is isomerized to exo-tetrahydrodicyclo-pentadiene, wherein the supported acidic ionic liquid includes a porous support and an acidic ionic liquid, and the acidic ionic liquid includes an aluminum halide, and a quaternary ammonium halide or a quaternary phosphonium halide. The porous support is impregnated with the acidic ionic liquid. Furthermore, under different reaction conditions, the exo-tetrahydrodicyclopentadiene product can be isomerized to adamantane in the presence of such a supported acidic ionic liquid.

20 Claims, No Drawings

PROCESS FOR ISOMERIZATION OF TETRAHYDRODICYCLOPENTADIENE USING SUPPORTED ACIDIC IONIC LIQUID AS A CATALYST

BACKGROUND OF THE INVENTION

1. Field of the Invention

The present invention generally relates to a process for isomerization of cycloalkane, and more particularly to a process for isomerization of tetrahydrodicyclopentadiene (THD-CPD) using a supported acidic ionic liquid as catalyst.

2. The Prior Arts

The acid catalysts have been used in petroleum and petrochemical industry for many years. For example the acid catalysts have been used in cracking, alkylation, isomerisation, polymerisation, etherification, sterification, amidation, and transesterification processes, and especially traditional Lewis acids ($AlCl_3$ and $ZnCl_2$) and Brönsted acids (HF and $H_2SO_4$) are often used as catalysts for alkylation and isomerisation. Although Lewis acids and Brönsted acids are effective in promoting the reaction, there are still a lot of problems to be overcome, such as product separation, catalyst recovery, facility corrosion, and treatment of spent acid catalyst and waste water. Solid acids or superacids have been investigated for the substitution of liquid acids, recently (Misono, M., CHEMTECH, November 23 (1993); Rao, P., Oil & Gas J., September 9, 56 (1996); Weitkamp, J., Catal. Today, 49, 193 (1999)).

One improved method is that anhydrous aluminum trichloride is directly supported on the inorganic carrier for the preparation of the supported Lewis acid catalysts, and such obtained supported Lewis acid catalysts exhibit high activity and selectivity for catalytic cracking of hydrocarbons, and the isomerization and alkylation of aromatic hydrocarbons (Getty, E. E., Inorg. Chem., 29, 1186 (1990); Hu, X., Appli. Catal., A: General, 217, 1 (2001). Drago et al. disclosed that it is preferable that the supported $AlCl_3$ catalyst is prepared using carbon tetrachloride ($CCl_4$) as a solvent (J. Am. Chem. Soc., 110, 3311 (1988)). Furthermore, the supported $AlCl_3$ catalysts exhibit high activity and selectivity when montmorillonite (Clark, J. H., J. Chem. Soc. Chem. Commun., 56, 2037(1995)), polymer (Fuentes, G. A., J. Catal., 78, 436 (1982)), and molecular sieve [Jun, S., J. Catal., 195, 237 (2000); Hu, X., J. Catal., 195, 412 (2000)] are used as a carrier. Moreover, the application of the supported $AlCl_3$ catalysts will become broader if the carrier selection, the catalyst supporting method, and the catalyst regeneration method can be improved ((Petrochemical Technology, 35(1), 88 (2006)).

Although the solid acid catalysts have many advantages, the acid sites in the solid acid catalysts are not easily accessible to reactants, and the proportion of the active sites is low. Furthermore, the catalyst activity is generally degraded at high reaction temperature due to the suppression of carbon deposit on the external surface of the catalyst. Therefore, the acidic ionic liquids are found to be a preferred alternative because of its adjustable properties, such as its acidity and solubility. Most of the ionic liquid catalysts are used in the liquid-liquid biphasic system, and thereby the reactants and the products are easily separated from the ionic liquid catalysts. The catalytic reaction can be effectively carried out due to the ionic liquid's non-volatile property and changeable acidity and solubility by changing the kinds of cation and anion and the molar ratio of cation and anion to aluminum trichloride. However, from the industrial point of view, the solid catalysts are considered to be the preferred ones because the products are easily separated and the fixed-bed reactor can be used. Although the liquid-liquid biphasic system has the advantages, a large amount of ionic liquid is required in use. In considering of economy and environmental protection, the supported ionic liquid systems are the preferred ones. The supported ionic liquid catalyst is in solid form, and however the active substance existing in ionic liquid supported on a solid surface. Therefore, the supported ionic liquid catalysts have the same reaction activity as that of the homogeneous catalysts.

The supported ionic liquid catalysts are prepared using the grafting or the impregnation methods, and in these two methods, the acidic ionic liquid is directly immobilized on $SiO_2$, $Al_2O_3$, or MCM-41, as support. In another method, the cation-halide from the ionic liquid is covalently bonded to the resin, which then reacts with $AlCl_3$ to form the supported acidic ionic liquid. In the other method, the —SiOH group on the silica formed by sol-gel technique is changed to —Si$(OEt)_3$ group attached to the cation of the ionic liquid, and then $AlCl_3$ is added to form the supported acidic ionic liquid (Journal of Petroleum, 41(4), 25(2005)). In most cases, BMIC-$AlCl_3$ ionic liquid is loaded on the support powder by impregnation technique, and BMIC represents 1-methyl-3-butylimidazolium chloride, and in this method, the impregnation process is fast, but HCl will be formed after BMIC-$AlCl_3$ ionic liquid reacts with the —OH group on the support surface, and the formed HCl will dissolve Al in BMIC-$AlCl_3$ (Castro, C. De, J. Catal. 196, 86 (2000)). However, this process suffer from major drawbacks: the action force between the ionic liquid and support is weak; and only partial of $AlCl_3$ species existing in the ionic liquid loaded on the support are involved in the catalytic reaction due to the destruction of the support structure. However, the above-mentioned problems can be overcome by using grafting method. For example, 1-(triethoxy-silyl)-propyl-3-methyl-imidazolium chloride-$AlCl_3$ reacts with the support in toluene by grafting technique to obtain the grafted acidic ionic liquid formed on the support (Volkenberg, M. H., Green Chem., 4, 88(2002); Sauvage, E., U.S. Pat. No. 6,969,693 B2 (2005); Kang, K. K., J. Chin. Inst. Chem. Engrs., 37(1), 17 (2006)). However, the —OH groups on the support can be first treated, and then the quaternary ammonium salt/$AlCl_3$ ionic liquid is impregnated into the support. Consequently, HCl will not be formed when the ionic liquid containing $AlCl_3$ is impregnated into the support, In U.S. Pat. No. 3,381,046, the endo-tetrahydrodicyclopentadiene (endo-THDCPD) is isomerized to exo-tetrahydrodicyclopentadiene (exo-THDCPD) in the presence of sulfuric acid. In U.S. Pat. No. 4,086,284, the endo-tetrahydrodicyclopentadiene is isomerized to exo-THDCPD in the presence of aluminum trichloride. However, the ring-opening, cleavage, polymerization reaction will occur with sulfuric acid, and thereby there are a lot of problems left to be tackled, such as by-product formation, black coke, facility corrosion, and treatment of spent acid. When aluminum trichloride is used as a catalyst, a washing of the exo-tetrahydrodicyclopentadiene is required to remove any remaining aluminum trichloride, and consequently a large amount of sludge waste is produced. Adamantane (tricyclo[3.3.1.1$^{3,7}$]decane) can be synthesized using aluminum trichloride, superacid, or REY zeolite as a catalyst, and there are still a lot of problems left to be tackled, such as reaction selectivity, and facility corrosion.

SUMMARY OF THE INVENTION

Accordingly, the objective of the present invention is to provide a process for isomerization of tetrahydrodicyclopentadiene using a supported acidic ionic liquid as catalyst in order to solve the problems of reaction selectivity, and facility corrosion.

To achieve the foregoing objective, the present invention provides a process for isomerization of tetrahydrodicyclopentadiene using a supported acidic ionic liquid as catalyst, comprising the following steps: (a) contacting endo-tetrahydrodicyclopentadiene with the supported acidic ionic liquid comprising a porous support impregnated with an acidic ionic liquid including at least one aluminum halide and at least one compound selected from the group consisting of quaternary ammonium halide, and quaternary phosphonium halide, wherein the molar ratio of the endo-tetrahydrodicyclopentadiene to the acidic ionic liquid is in the range of from 100:1 to 1:10, and the contacting temperature is in the range of from 40° C. to 70° C.; (b) continuing the contacting until at least a portion of the endo-tetrahydrodicyclopentadiene is isomerized to exo-tetrahydrodicyclopentadiene; (c) and separating the exo-tetrahydrodicyclopentadiene from the contacting materials.

Under different reaction conditions, the newly formed exo-tetrahydrodicyclopentadiene can further contact with the supported acidic ionic liquid, and thereby at least a portion of the exo-tetrahydrodicyclopentadiene is isomerized to adamantane wherein the molar ratio of the exo-tetrahydrodicyclopentadiene to the acidic ionic liquid is in the range of from 100:1 to 1:10, and the contacting temperature is in the range of from 60° C. to 90° C. adamantane.

The exo-tetrahydrodicyclopentadiene can be effectively isomerized to adamantane by using the supported acidic ionic liquid of the present invention. Adamantane is a cycloalkane with three condenced cyclohexane rings in chair conformation. This diamond-like structure is hard but unstrained. That is why adamantane have an extremely high thermal stability (up to 660° C.). The tertiary hydrogen of adamantane can be substituted by nucleophilic (SN1-type) or electrophilic (SE2-type) substitution reactions to form many useful adamantane derivatives. Adamantane derivatives are useful in medicine, e.g. amantadine, memantine, and rimantadine. Condensed adamantanes or diamondoids have been isolated from petroleum fractions, where they occur in small amounts. These species are of interest as molecular approximations of the cubic diamond framework, terminated with C—H bonds. 1,3-dehydroadamantane is a member of the propellane family.

The advantage of the present invention is that when the supported acidic ionic liquid as catalyst of the present invention is used in the process for isomerization of tetrahydrodicyclopentadiene, high reaction conversion rate and high reaction selectivity can be achieved. Also, the problems of spent acid, and facility corrosion can be solved.

The foregoing and other objects, features, aspects and advantages of the present invention will become better understood from a careful reading of a detailed description provided herein below.

DETAILED DESCRIPTION OF THE PREFERRED EMBODIMENTS

In the present invention, the solid endo-tetrahydrodicyclopentadiene can be effectively isomerized to the liquid exo-tetrahydrodicyclopentadiene, namely JP-10 (a current missile fuel, chemical formula $C_{10}H_{16}$), by using the supported acidic ionic liquid of the present invention, wherein endo-tetrahydrodicyclopentadiene is obtained by hydrogenation of dicyclopentadiene (DCPD) present as by-products in the steam cracking process in ethylene plants. Subsequently, the solid endo-tetrahydrodicyclopentadiene is catalytically isomerized to the liquid exo-tetrahydrodicyclopentadiene, namely JP-10 (a current missile fuel, chemical formula $C_{10}H_{16}$), and then exo-tetrahydrodicyclopentadiene is further catalytically isomerized to adamantane. These reactions are shown below:

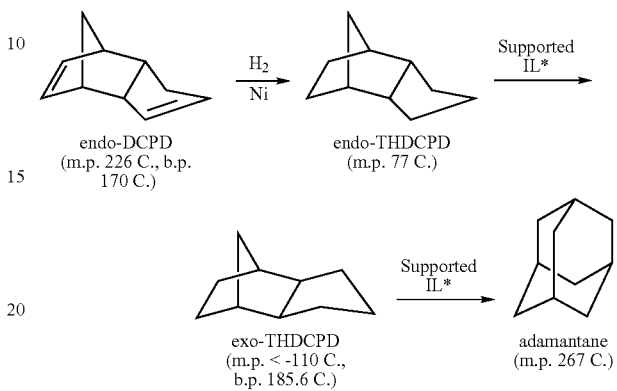

endo-DCPD (m.p. 226 C., b.p. 170 C.)
endo-THDCPD (m.p. 77 C.)
exo-THDCPD (m.p. < -110 C., b.p. 185.6 C.)
adamantane (m.p. 267 C.)

*IL = [R'NR$_3$]$^+$AlCl$_4^-$

The present invention provides a process for isomerization of tetrahydrodicyclopentadiene using a supported acidic ionic liquid as catalyst, comprising the following steps: (a) endo-tetrahydrodicyclopentadiene is contacted with the supported acidic ionic liquid, wherein the supported acidic ionic liquid comprises a porous support impregnated and an acidic ionic liquid, and the acidic ionic liquid includes at least one aluminum halide and at least one compound selected from the group consisting of quaternary ammonium halide, and quaternary phosphonium halide, wherein the molar ratio of the endo-tetrahydrodicyclopentadiene to the acidic ionic liquid is in the range of from 100:1 to 1:10, preferably from 10:1 to 1:5, and the contacting temperature is in the range of from 25° C. to 150° C., preferably from 40° C. to 70° C.; (b) continuing the contacting until at least a portion of the endo-tetrahydrodicyclopentadiene is isomerized to exo-tetrahydrodicyclopentadiene, wherein the contacting time is in a range of from 0.1 to 24 hours; (c) and recovering the exo-tetrahydrodicyclopentadiene.

Under different reaction conditions, the newly formed exo-tetrahydrodicyclopentadiene can be further contacted with the same supported acidic ionic liquid as above, wherein the molar ratio of the exo-tetrahydrodicyclopentadiene to the acidic ionic liquid is in the range of from 100:1 to 1:10, preferably from 10:1 to 1:5, and the contacting temperature is in the range of from 25° C. to 150° C., preferably from 60° C. to 90° C., and the contacting time is in a range of from 0.1 to 48 hours.

The acidic ionic liquid used in the present invention comprises at least one aluminum halide and at least one compound selected from the group consisting of quaternary ammonium halide [R'NR$_3$]$^+$X$^-$ and quaternary phosphonium halide [R'PR$_3$]$^+$X$^-$, and Examples of the quaternary cations, [R'NR$_3$]$^+$X$^-$ or [R'PR$_3$]$^+$X$^-$, include but are not limited to tetraalkylammonium, dialkylpyridinium, trialkylimidazolium, and tetraalkylphosphonium, which are represented by structural formulas as follows:

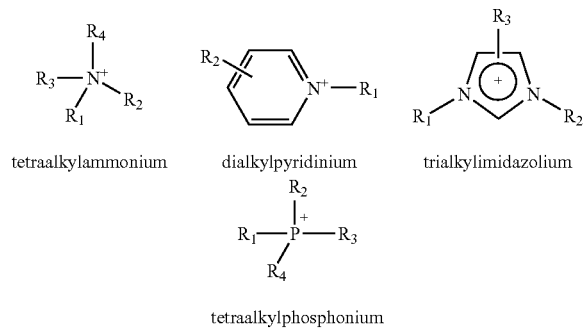

tetraalkylammonium    dialkylpyridinium    trialkylimidazolium tetraalkylphosphonium wherein each of the alkyl groups of tetraalkylammonium, dialkylpyridinium, and trialkylimidazolium is represented by $C_nH_{2n+1}$, where n is an integer from 0 to 18. The halide ions used in the present invention are selected from the group consisting of chloride, bromide, and iodide ions.

The aluminum halide used in the present invention is selected from the group consisting of aluminum trichloride, and aluminum tribromide.

The porous support used in the present invention is a porous metal oxide selected from the group consisting of $SiO_2$, $Al_2O_3$, MCM-41, and montmorillonite. The porous support has a BET surface area of 10 to 1500 m²/g, and has an average pore diameter of 10 to 200 Å.

The porous support used in the present invention can be directly impregnated with the acidic ionic liquid. Alternatively, the acidic ionic liquid can be first dispersed in $CCl_4$, $CHCl_3$, $CH_2Cl_2$, or $C_2H_4Cl_2$ solvent, and then the porous support is impregnated with the resulting solution. The weight ratio of the acidic ionic liquid to the porous support is in the range of from 0.1:1 to 4.0:1, and preferably from 0.8:1 to 2.0:1.

In order to remove —OH groups on the surface of the porous support, the porous support used in the present invention can be treated with a surface treating agent. Examples of the surface treating agent include Lewis acids, such as $R_nAlX_{3-n}$ (n is an integer from 0 to 2), $R_nSnX_{4-n}$ (n is an integer from 0 to 3), $R_nZnX_{2-n}$ (n is an integer from 0 to 1), or $R_nFeX_{3-n}$ (n is an integer from 0 to 2); and organic silicon halides, such as $R_nSiX_{4-n}$ (n is an integer from 0 to 3), where $R=C_1-C_{18}$ alkyl groups, and X=F, Cl, Br or I. The weight ratio of the surface treating agent to the porous support is 0.1:5.0, and preferably from 0.3:0.8. Alternatively, the surface treating agent can be first dissolved in hydrocarbon compounds, chloride-containing compounds, or ionic liquids as solvent, then the porous support is treated with the resulting solution.

Preparation of an Acidic Ionic Liquid and a Supported Acidic Ionic Liquid

In a nitrogen-filled glove-box, alkyl nitride, alkyl bromide, and aluminum trichloride are weighted, and successively introduced into a two-necked, round-bottomed flask provided with a magnetic stir bar and a three-way stopcock. The ionic liquid is obtained by homogeneously mixing alkyl nitride, alkyl bromide, and aluminum trichloride. Subsequently, an appropriate amount of dichloromethane is introduced into the two-necked, round-bottomed flask, and homogeneously mixed with the obtained ionic liquid therein, followed by introduction of an appropriate amount of support so that the support is in the 'wetting state'. Then, dichloromethane is pumped off under nitrogen. Furthermore, the two-necked, round-bottomed flask containing the supported acidic ionic liquid is taken out from the nitrogen-filled glove-box. Thereafter, the two-necked, round-bottomed flask containing the supported acidic ionic liquid is equipped with a condenser and charged with the reactant (endo-tetrahydrodicyclopentadiene or exo-tetrahydrodicyclopentadiene dissolved in cyclohexane) by using syringe under nitrogen and the reaction mixture is heated at a desired temperature in a hot oil bath, while stirring at 400 rpm, and during the reaction, the samples are taken after a certain period of time, and analyzed by HP6890 Series gas chromatograph equipped with a Chrompack CP-Sil-5CB column and an automatic injection system. Moreover, the support used in the above-mentioned preparation process of the present invention is first treated with a surface treating agent in order to remove —OH groups on the surface of the support before use. That is, an appropriate amount of $AlCl_3$ or $(CH_3)_3SiCl$ is dissolved in tetrachloromethane, trichloromethane, dichloromethane, dichloroethane, benzene, or toluene. Then, the support is added to the resulting solution, which is then refluxed for 24 hours, followed by filtering and drying in vacuum to obtain the surface treated support.

The following examples illustrate the invention without limiting its scope.

Example 1

Support Effect

In embodiment 1, in a nitrogen-filled glove-box, 0.529 g (0.00458 mole) of pyridine hydrochloride (PHC) and 1.134 g (0.0085 mole) of aluminum trichloride are weighted, and successively introduced into a two-necked, round-bottomed flask provided with a magnetic stir bar. Then, the ionic liquid is obtained by homogeneously mixing pyridine hydrochloride and aluminum trichloride. Subsequently, 0.6 g of $SiO_2$ powder (80-120 mesh) as support is added to the obtained ionic liquid while stirring so that the support is in the 'wetting state'. Then, the two-necked, round-bottomed flask containing the supported acidic ionic liquid is taken out from the nitrogen-filled glove-box. Thereafter, the two-necked, round-bottomed flask containing the supported acidic ionic liquid is equipped with a condenser under nitrogen, and the reactant (cyclohexane/endo-tetrahydrodicyclopentadiene, and the volume ratio of cyclohexane/endo-tetrahydrodicyclopentadiene is 1/1) are injected in the two-necked, round-bottomed flask by using syringe, and the reaction mixture is heated at 50° C. in a hot oil bath while stirring at 400 rpm in order to carry out the isomerization reaction, and during the isomerization reaction, samples are taken after half an hour, then one hour then 2 then 6 hours thereafter, and analyzed by HP6890 Series gas chromatograph. The results show that the reaction conversion rates are 65.1%, 81.3%, 94.5%, and 98.9% after reacting for half an hour, one hour, 2 hours, and 6 hours, respectively. The selectivity of exo-tetrahydrodicyclopentadiene can reach 100%.

In embodiments 2, 3, and 4, the supported acidic ionic liquids are prepared by the same method as the above embodiment 1 and also the isomerization reactions are carried out under the same conditions as the above embodiment 1 except that none of $SiO_2$ powder, 1.2 g of $SiO_2$ powder, and 1.8 g of $SiO_2$ powder are used as a support, respectively, instead of 0.6 g of $SiO_2$ powder. Table 1 shows the results of the conversion rate of endo-tetrahydrodicyclopentadiene to exo-tetrahydrodicyclopentadiene using the supported acidic ionic liquid of the present invention as catalyst after a certain period of time.

TABLE 1

| | | Embodiment | | | |
|---|---|---|---|---|---|
| | | 1 | 2 | 3 | 4 |
| The amount of SiO$_2$ used | | 0.6 g | 0 g | 1.2 g | 1.8 g |
| Reaction time and the conversion rate of endo-THDCPD (%) | 0.5 hr | 65.1 | 62.5 | 86.4 | 70.1 |
| | 1 hr | 84.3 | 83.5 | 96.2 | 86.8 |
| | 2 hr | 96.5 | 96.6 | 98.8 | 95.4 |
| | 6 hr | 98.9 | 99.0 | 99.1 | 98.2 |

From Table 1 it knows that when 1.2 g of SiO$_2$ is used (in embodiment 3), the conversion rate of endo-tetrahydrodicyclopentadiene is the best one. Therefore, an appropriate amount of SiO$_2$ is required for high conversion rate of endo-tetrahydrodicyclopentadiene. Accordingly, the support effect on the conversion rate of endo-tetrahydrodicyclopentadiene to exo-tetrahydrodicyclopentadiene exists.

Example 2
Effect of the Surface Treatment on the Support

The supported acidic ionic liquid is prepared by the same method as in EXAMPLE 1 except that SiO$_2$ powder is treated with AlCl$_3$ as surface treating agent in order to remove —OH groups on the surface of SiO$_2$ powder before SiO$_2$ powder as support is impregnated with the obtained ionic liquid, wherein the —OH groups on the surface of SiO$_2$ powder can deactivate the activity of the acidic ionic liquid. 0.3 g of AlCl$_3$ and 5 ml of CH$_2$Cl$_2$ are added onto 1.2 g of dry SiO$_2$ powder as support while stirring, and after stirring for 1 hour, SiO$_2$ powder is separated from AlCl$_3$, and washed with a large amount of CH$_2$Cl$_2$ for many times. Then, CH$_2$Cl$_2$ is pumped off. After that, the treated SiO$_2$ powder is added to the ionic liquid prepared as EXAMPLE 1 to form the supported acidic ionic liquid. Subsequently, the solid endo-tetrahydrodicyclopentadiene is isomerized to the liquid exo-tetrahydrodicyclopentadiene using the newly formed supported acidic ionic liquid, and the isomerization activity of the newly formed supported acidic ionic liquid is determined (embodiments 5 and 6) and listed in Table 2.

TABLE 2

| | | Embodiment | |
|---|---|---|---|
| | | 5 | 6 |
| The amount of SiO$_2$ used | | 1.2 g | 1.2 g |
| Pretreatment of the support | The amount of CH$_2$Cl$_2$ used | 0 ml | 5 ml |
| | The amount of AlCl$_3$ used | 0 g | 0.3 g |
| CH$_2$Cl$_2$ used for impregnation | | 5 ml | 5 ml |
| Reaction time and the conversion rate of endo-THDCPD (%) | 0.5 hr | 48.3 | 61.2 |
| | 1 hr | 63.2 | 77.6 |
| | 2 hr | 80.7 | 96.4 |
| | 6 hr | 97.2 | 98.4 |

From Table 2 it knows that if SiO$_2$ powder is treated with AlCl$_3$ as surface treating agent before SiO$_2$ powder is impregnated with ionic liquid, the deactivity of the acidic ionic liquid can be diminished.

Moreover, (CH$_3$)$_3$SiCl can be used as surface treating agent instead of AlCl$_3$ used as surface treating agent as described above. (CH$_3$)$_3$SiCl can react with —SiOH on the surface of SiO$_2$ to form HCl and —SiO—Si(CH$_3$)$_3$. In the embodiment 7, 0.6 g of (CH$_3$)$_3$SiCl is used as surface treating agent instead of 0.3 g of AlCl$_3$. In the embodiment 8, SiO$_2$ powder and (CH$_3$)$_3$SiCl are refluxed in cyclohexane for 4 hours, and then SiO$_2$ powder is separated from the remaining liquid, and washed with a large amount of CH$_2$Cl$_2$ for many times. Then, CH$_2$Cl$_2$ is pumped off. Thereafter, the treated SiO$_2$ powder is impregnated with the ionic liquid prepared as EXAMPLE 1 to form the supported acidic ionic liquid. Subsequently, the solid endo-tetrahydrodicyclopentadiene is isomerized to the liquid exo-tetrahydrodicyclopentadiene using the newly formed supported acidic ionic liquid, and the isomerization activity of the newly formed supported acidic ionic liquid is determined (embodiment 8). Moreover, 0.3 g of AlCl$_3$ can be dissolved in the ionic liquid, such as hexyl-3-methylimidazolium chloride (HMIC) or pyridine hydrochloride (PHC), used as solvent instead of CH$_2$Cl$_2$. 0.3 g of AlCl$_3$ dissolved in PHC is stirred with the support so as to allow AlCl$_3$ to enter the pores of the SiO$_2$ powder for the surface treatment. Then, SiO$_2$ powder is washed with a large amount of CH$_2$Cl$_2$ for many times. Thereafter, CH$_2$Cl$_2$ is pumped off. The treated SiO$_2$ powder is impregnated with the ionic liquid prepared as EXAMPLE 1 to form the supported acidic ionic liquid. Subsequently, the solid endo-tetrahydrodicyclopentadiene is isomerized to the liquid exo-tetrahydrodicyclopentadiene using the newly formed supported acidic ionic liquid, and the isomerization activity of the newly formed supported acidic ionic liquid is determined (embodiment 9). The results are listed in Table 3.

TABLE 3

| | | Embodiment | | | | |
|---|---|---|---|---|---|---|
| | | 5 | 6 | 7 | 8 | 9 |
| The amount of SiO$_2$ used | | 1.2 g | 1.2 g | 1.2 g | 1.2 g | 1.2 g |
| Pretreatment of the support | The amount of CH$_2$Cl$_2$ used | 0 ml | 5 ml | 5 ml | 0 ml | 5 ml |
| | The amount of cyclohexane used | 0 ml | 0 ml | 0 ml | 10 ml | 0 ml |
| | The amount of PHC used | 0 g | 0 g | 0 g | 0 g | 0.13 g |
| | The amount of AlCl$_3$ used | 0 g | 0.3 g | 0 g | 0 g | 0.3 g |
| | The amount of (CH$_3$)$_3$SiCl used | 0 g | 0 g | 0.6 g | 0.6 g | 0 g |
| CH$_2$Cl$_2$ used for impregnation | | 5 ml | 5 ml | 5 ml | 5 ml | 5 ml |
| Reaction time and the conversion rate of endo-THDCPD (%) | 0.5 hr | 48.3 | 61.2 | 63.8 | 73.5 | 82.5 |
| | 1 hr | 63.2 | 77.6 | 79.9 | 89.0 | 94.8 |
| | 2 hr | 80.7 | 96.4 | 91.1 | 95.9 | 98.2 |
| | 6 hr | 97.2 | 98.4 | 98.9 | 99.0 | 99.2 |

From Table 3 it knows that if $SiO_2$ powder is treated with $AlCl_3$ or $(CH_3)_3SiCl$ as surface treating agent before $SiO_2$ powder is impregnated with ionic liquid, the deactivity of the acidic ionic liquid can be diminished. Among them, the effect of pretreatment of the support on catalytic activity is better when $AlCl_3$ is dissolved in PHC, or the support is refluxed with $(CH_3)_3SiCl$.

Example 3

Effect of Kinds of the Supports

The supported acidic ionic liquid is prepared by the same method as in EXAMPLE 1 except that $Al_2O_3$ (135 m$^2$/g of BET surface area, and 60 Å of average pore diameter), MCM-41 (1023 m$^2$/g of BET surface area, and 35 Å of average pore diameter), and montmorillonite (200 m$^2$/g of BET surface area, and 12 Å of average pore diameter) are used as support instead of $SiO_2$ (277 m$^2$/g of BET surface area, and 95 Å of average pore diameter) in embodiments 10, 11 and 12, respectively. Moreover, the surface of the support is treated with $(CH_3)_3SiCl$ in accordance with EXAMPLE 2. The results are listed in Table 4.

TABLE 4

| | | Embodiment | | | |
| --- | --- | --- | --- | --- | --- |
| | | 9 | 10 | 11 | 12 |
| Support | | $SiO_2$ | $Al_2O_3$ | MCM-41 | Montmorillonite |
| Pretreatment of the support | The amount of cyclohexane used | 10 ml | 10 ml | 10 ml | 10 ml |
| | The amount of $(CH_3)_3SiCl$ used | 0.6 g | 0.6 g | 0.6 g | 0.6 g |
| $CH_2Cl_2$ used for impregnation | | 5 ml | 5 ml | 5 ml | 5 ml |
| Reaction time and the conversion rate of endo-THDCPD (%) | 0.5 hr | 73.5 | 74.3 | 76.0 | 11.9 |
| | 1 hr | 89.0 | 86.3 | 85.5 | 21.3 |
| | 2 hr | 95.9 | 93.6 | 93.5 | 39.7 |
| | 6 hr | 99.0 | 98.5 | 97.7 | 77.2 |

From Table 4 it knows that when montmorillonite is used as support, the conversion rate of endo-tetrahydrodicyclopentadiene is the lowest.

Example 4

Effect of Reaction Temperature

In a nitrogen-filled glove-box, 7.5 g of aluminum trichloride is dissolved in 3.7 g of pyridine hydrochloride in a round-bottomed flask, and then 20 ml of $CH_2Cl_2$ is added thereto to obtain the surface treating agent. 3.8 g of montmorillonite and the obtained surface treating agent are mixed for 30 minutes, and the pretreated montmorillonite is washed with a large amount of $CH_2Cl_2$ for many times. In addition, in another round-bottomed flask, 0.529 g (0.00458 mole) of pyridine hydrochloride and 1.134 g (0.0085 mole) of aluminum trichloride are homogeneously mixed together, followed by adding 5 ml of $CH_2Cl_2$ thereto, and thereby the acidic ionic liquid is obtained. Afterwards, the pretreated montmorillonite is added to the acidic ionic liquid while stirring so that the montmorillonite is in the 'wetting state'. Then, the round-bottomed flask containing the supported acidic ionic liquid is taken out from the nitrogen-filled glove-box. Then, $CH_2Cl_2$ contained in the round-bottomed flask is evacuated under vacuum of 300 torr. Subsequently, 16 g of the reactant (cyclohexane/endo-tetrahydrodicyclopentadiene, and the volume ratio of cyclohexane/endo-tetrahydrodicyclopentadiene is 1/1) are injected in the round-bottomed flask by using syringe, and the reaction mixture is heated at 50° C. in a hot oil bath, while stirring at 600 rpm in order to carry out the isomerization reaction, and during the isomerization reaction, samples are taken after a certain period of time, and analyzed by HP6890 Series gas chromatograph equipped with a Chrompack CP-Sil-5CB column and an automatic injection system. The results show that the isomerization conversion rates of endo-tetrahydrodicyclopentadiene are 71.7% (embodiment 13), 77.0% (embodiment 14), and 93.7% (embodiment 15) after reacting for one hour at the temperature of 40° C., 50° C., and 60° C., respectively, and the selectivities of exo-tetrahydrodicyclopentadiene are 100% (embodiment 13), 100% (embodiment 14), and 99.6% (embodiment 15), respectively.

TABLE 5

| | Embodiment | | |
| --- | --- | --- | --- |
| | 13 | 14 | 15 |
| Reaction temperature | 40° C., | 50° C., | 60° C., |
| The conversion rate of endo-THDCPD (%) | 71.7 | 77.0 | 93.7 |
| The selectivity of exo-THDCPD product (%) | 100 | 100 | 99.6 |

Example 5

Effect of Kinds of Ionic Liquids

The pretreated montmorillonite obtained by the same method as EXAMPLE 4 is impregnated into the acidic ionic liquid consisting of 0.529 g (0.00458 mole) of pyridine hydrochloride, 1.134 g (0.0085 mole) of aluminum trichloride, and 5 ml of $CH_2Cl_2$ in the round-bottomed flask, and then $CH_2Cl_2$ is evacuated. Subsequently, 16 g of the reactant (cyclohexane/endo-tetrahydrodicyclopentadiene, and the volume ratio of cyclohexane/endo-tetrahydrodicyclopentadiene is 1/1) are injected in the round-bottomed flask by using syringe, and the reaction mixture is heated at 50° C. in a hot oil bath while stirring at 600 rpm in order to carry out the isomerization reaction. The results show that the isomerization conversion rate of endo-tetrahydrodicyclopentadiene is 94.5% after reacting for six hours, and the selectivity of exo-tetrahydrodicyclopentadiene is 100% (embodiment 16).

In addition, two different acidic ionic liquids are prepared by mixing 0.63 g (0.00458 mole) of triethylamine hydrochloride (TEAC)/1.134 g (0.0085 mole) of $AlCl_3$/5 ml of $CH_2Cl_2$, and by mixing 0.8 g (0.00458 mole) of butyl methyl imidazolium chloride (BMIC)/1.134 g (0.0085 mole) of $AlCl_3$/5 ml of $CH_2Cl_2$ in two separated round-bottomed flasks, respectively. Afterwards, the pretreated montmorillonites are respectively impregnated into the two different acidic ionic liquids. Subsequently, 16 g of the reactants (cyclohexane/endo-tetrahydrodicyclopentadiene, and the volume ratio of cyclohexane/endo-tetrahydrodicyclopentadiene is 1/1) are respectively injected in the two separated round-bottomed flasks by using syringe, and the two different reaction mixtures respectively contained in the two separated round-bottomed flasks are heated at 50° C. in a hot oil bath while stirring at 600 rpm in order to carry out the isomerization reaction. The results show that after reacting for six hours, the isomerization conversion rate of endo-tetrahydrodicyclopentadiene is 93.8%, and the selectivity of exo-tetrahydrodicyclopentadiene is 100% (in the case of triethylamine hydrochloride used for forming the acidic ionic liquid, embodiment 17); and the isomerization conversion rate of endo-tetrahydrodicyclopentadiene is 53.8%, and the selectivity of exo-tetrahydrodicyclopentadiene is 99.9% (in the case of butyl methyl imidazolium chloride used for forming the acidic ionic liquid, embodiment 18).

TABLE 6

|  | Embodiment | | |
|---|---|---|---|
|  | 16 | 17 | 18 |
| Base used for forming ionic liquid | PHC | TEAC | BMIC |
| The conversion rate of endo-THDCPD (%) | 94.5 | 93.8 | 53.8 |
| The selectivity of exo-THDCPD product (%) | 100 | 100 | 99.9 |

Example 6

Effect of the Amount of Ionic Liquids Used as Catalyst

In a nitrogen-filled glove-box, two different acidic ionic liquids are prepared by mixing 0.4 g (0.00229 mole) of 1-butyl-3-methylimidazolium chloride and 0.458 g (0.00343 mole) of aluminum trichloride, and by mixing 8 g (0.0458 mole) of 1-butyl-3-methylimidazolium chloride and 9.16 g (0.0687 mole) of aluminum trichlorid in the two separated round-bottomed flasks, respectively. Subsequently, 16 g of endo-tetrahydrodicyclopentadiene dissolved in heptane (the molar ratios of the acidic ionic liquid to the reactant are 1/25.6, 1/12.8, and 1/1.28, respectively) are respectively injected into the acidic ionic liquid by using syringe under nitrogen, and the different reaction mixtures are heated at 50° C. in a hot oil bath while stirring at 400 rpm in order to carry out the isomerization reaction.

The results show that after reacting for six hours, the isomerization conversion rate of endo-tetrahydrodicyclopentadiene is 36.2%, and the selectivity of exo-tetrahydrodicyclopentadiene is 100% (in the case of 1/25.6 of molar ratio of the acidic ionic liquid to the reactant, embodiment 19); the isomerization conversion rate of endo-tetrahydrodicyclopentadiene is 81.1%, and the selectivity of exo-tetrahydrodicyclopentadiene is 100% (in the case of 1/12.8 of molar ratio of the acidic ionic liquid to the reactant, embodiment 20); and the isomerization conversion rate of endo-tetrahydrodicyclopentadiene is 99.2%, and the selectivity of exo-tetrahydrodicyclopentadiene is 100% (in the case of 1/1.28 of molar ratio of the acidic ionic liquid to the reactant, embodiment 21). The results are listed in Table 7.

TABLE 7

|  | Embodiment | | |
|---|---|---|---|
|  | 19 | 20 | 21 |
| Molar ratio of the acidic ionic liquid to the reactant | 1/25.6 | 1/12.8 | 1/1.28 |
| The conversion rate of endo-THDCPD (%) | 36.2 | 81.1 | 99.2 |
| The selectivity of exo-THDCPD product (%) | 100 | 100 | 100 |

Example 7

Activity of Adamantane Formation

The supported acidic ionic liquid is prepared by using PHC, $AlCl_3$ (molar fraction=0.65), and $SiO_2$ in accordance with embodiment 9. The exo-tetrahydrodicyclopentadiene (JP-10) is used as a reactant in this example. The molar ratio of the acidic ionic liquid to the exo-tetrahydrodicyclopentadiene is 1:2.56. The isomerization reaction is carried out for about 24 hours at 70° C. The results are listed in Table 8.

TABLE 8

|  |  | Reaction time, hr | | | | |
|---|---|---|---|---|---|---|
|  |  | 1 | 4 | 6 | 12 | 24 |
| The conversion rate of exo-THDCPD (%) |  | 4.9 | 16.4 | 18.0 | 24.0 | 30.3 |
| The selectivity of product (%) | adamantane | 100 | 73.9 | 73.8 | 75.1 | 76.4 |
|  | decalin | 0 | 26.1 | 26.2 | 24.9 | 23.6 |

Example 8

Stability of Supported Acidic Ionic Liquid

The $SiO_2$ support is treated with $(CH_3)_3SiCl$, and then refluxed in cyclohexane for 4 hours. Afterwards, the supported acidic ionic liquid is prepared by the same method as described in example 1. Then, the first isomerization reaction of endo-tetrahydrodicyclopentadiene is carried out for 6 hours using the prepared supported acidic ionic liquid as catalyst, and then the conversion rate of endo-tetrahydrodicyclopentadiene is determined by HP6890 Series gas chromatograph equipped with a Chrompack CP-Sil-5CB column and an automatic injection system. Subsequently, the second isomerization reaction of endo-tetrahydrodicyclopentadiene is carried out for 6 hours using the supported acidic ionic liquid which was used in the first isomerization reaction, and then the conversion rate of endo-tetrahydrodicyclopentadiene is determined. Furthermore, the third isomerization reaction of endo-tetrahydrodicyclopentadiene is carried out for 6 hours using the supported acidic ionic liquid which was used in the first and second isomerization reactions, and then the conversion rate of endo-tetrahydrodicyclopentadiene is determined. The supported acidic ionic liquid of the present invention can keep activity at 95% or more even after three times of isomerization reactions. Therefore, the stability of the supported acidic ionic liquid of the present invention as catalyst is excellent.

It will be apparent to those skilled in the art that various modifications and variations can be made in the present invention without departing from the spirit or scope of the present invention. Thus, it is intended that the present invention cover the modifications and the variations of this invention provided they come within the scope of the appended claims and their equivalents.

What is claimed is:

1. A process for isomerization of tetrahydrodicyclopentadiene using a supported acidic ionic liquid as catalyst, comprising the following steps:
   (a) contacting endo-tetrahydrodicyclopentadiene with the supported acidic ionic liquid comprising a porous support impregnated with an acidic ionic liquid including at least one aluminum halide and at least one compound selected from the group consisting of quaternary ammonium halide and quaternary phosphonium halide, wherein a molar ratio of the endo-tetrahydrodicyclopentadiene to the acidic ionic liquid is in the range of from 100:1 to 1:10, and the contacting temperature is in the range of from 40° C. to 70° C.
   (b) continuing the contacting until at least a portion of the endo-tetrahydrodicyclopentadiene is isomerized to exo-tetrahydrodicyclopentadiene; and
   (c) recovering the exo-tetrahydrodicyclopentadiene.

2. The process according to claim 1, further comprising: contacting the exo-tetrahydrodicyclopentadiene with the supported acidic ionic liquid thereby isomerizing at least a portion of the exo-tetrahydrodicyclopentadiene to adamantane wherein a molar ratio of the exo-tetrahydrodicyclopentadiene to the acidic ionic liquid is in the range of from 100:1 to 1:10, and the contacting temperature is in the range of from 60° C. to 90° C.

3. The process according to claim 1, wherein the aluminum halide is selected from the group consisting of aluminum trichloride, and aluminum tribromide.

4. The process according to claim 1, wherein a salt cation of the quaternary ammonium halide is selected from the group consisting of tetraalkylammonium, dialkylpyridinium, and trialkylimidazolium ions, and a salt anion of the quaternary phosphonium halide is selected from the group consisting of chloride, bromide, and iodide ions, wherein each of the alkyl groups of tetraalkylammonium, dialkylpyridinium, and trialkylimidazolium represented by $C_nH_{2n+1}$, where n is an integer from 0 to 18.

5. The process according to claim 1, wherein a salt cation of the quaternary phosphonium halide is tetraalkylphosphonium, and a salt anion of the quaternary phosphonium halide is selected from the group consisting of chloride, bromide, and iodide ions, wherein each of the alkyl groups of the tetraalkylphosphonium is represented by $C_nH_{2n+1}$, where n is an integer from 0 to 18.

6. The process according to claim 1, wherein the molar ratio of the endo-tetrahydrodicyclopentadiene to the acidic ionic liquid is in the range of from 10:1 to 1:5.

7. The process according to claim 2, wherein the molar ratio of the exo-tetrahydrodicyclopentadiene to the acidic ionic liquid is in the range of from 10:1 to 1:5.

8. The process according to claim 1, wherein the porous support is a porous metal oxide.

9. The process according to claim 1, wherein the porous support is selected from the group consisting of $SiO_2$, $Al_2O_3$, MCM-41, and montmorillonite.

10. The process according to claim 1, wherein the weight ratio of the acidic ionic liquid to the porous support is in the range of from 0.1:1 to 4.0:1.

11. The process according to claim 1, wherein the weight ratio of the acidic ionic liquid to the porous support is in the range of from 0.8:1 to 2.0:1.

12. The process according to claim 1, wherein the contacting time is in a range of from 0.1 to 24 hours.

13. The process according to claim 1, wherein the contacting time is in a range of from 0.1 to 48 hours.

14. The process according to claim 1, wherein the porous support is treated with a surface treating agent including one of $R_nAlX_{3-n}$ (n is an integer from 0 to 2), $R_nSnX_{4-n}$ (n is an integer from 0 to 3), $R_nZnX_{2-n}$ (n is an integer from 0 to 1), $R_nFeX_{3-n}$ (n is an integer from 0 to 2), and $R_nSiX_{4-n}$ (n is an integer from 0 to 3), where R=$C_1$-$C_{18}$ alkyl groups, and X=F, Cl, Br or I, in order to remove —OH groups on the surface of the porous support.

15. The process according to claim 14, wherein the weight ratio of the surface treating agent to the porous support is 0.1:5.0.

16. The process according to claim 14, wherein the weight ratio of the surface treating agent to the porous support is 0.3:0.8.

17. The process according to claim 14, wherein the porous support is treated with the surface treating agent dissolved in hydrocarbon compounds, chloride-containing compounds, or ionic liquids as solvent.

18. The process according to claim 1, wherein the porous support is directly impregnated with the acidic ionic liquid.

19. The process according to claim 1, wherein the porous support has a BET surface area of 10 to 1500 $m^2/g$.

20. The process according to claim 1, wherein the porous support has an average pore diameter of 10 to 200 Å.

* * * * *